US009067877B2

(12) United States Patent
Bonrath et al.

(10) Patent No.: US 9,067,877 B2
(45) Date of Patent: Jun. 30, 2015

(54) PROCESS FOR THE PRODUCTION OF 1,3,3-TRIMETHYL-2-(3-METHYLPENT-2-EN-4-YNYL)CYCLOHEX-1-ENE

(75) Inventors: Werner Bonrath, Basel (CH); Thomas Netscher, Basel (CH); Jan Schütz, Basel (CH); Bettina Wüstenberg, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/128,741

(22) PCT Filed: Jun. 14, 2012

(86) PCT No.: PCT/EP2012/061280
§ 371 (c)(1),
(2), (4) Date: May 28, 2014

(87) PCT Pub. No.: WO2012/175396
PCT Pub. Date: Dec. 27, 2012

(65) Prior Publication Data
US 2014/0323767 A1  Oct. 30, 2014

(30) Foreign Application Priority Data
Jun. 22, 2011 (EP) .................................... 11171068

(51) Int. Cl.
C07C 1/24 (2006.01)
C07C 403/02 (2006.01)
C07C 403/16 (2006.01)
C07C 403/08 (2006.01)
C07C 403/24 (2006.01)

(52) U.S. Cl.
CPC ................. *C07C 403/02* (2013.01); *C07C 1/24* (2013.01); *C07C 403/16* (2013.01); *C07C 2101/16* (2013.01); *C07C 403/08* (2013.01); *C07C 403/24* (2013.01)

(58) Field of Classification Search
CPC ........................................................ C07C 1/24
USPC .................................... 585/23, 357, 534, 639
See application file for complete search history.

(56) References Cited

FOREIGN PATENT DOCUMENTS

GB        1 034 189        6/1966

OTHER PUBLICATIONS

Lopez et al. Structural Effects Affecting the Thermal Electrocyclic Ring Closure of Vinylallenes to Alkylidenecyclobutenes. Journal of the American Chemical Society, 1996, vol. 118, pp. 1881-1891.*
International Search Report for PCT/EP2012/061280, mailed Sep. 20, 2012.

* cited by examiner

*Primary Examiner* — Sikarl Witherspoon
(74) *Attorney, Agent, or Firm* — Nixon & Vanderhye P.C.

(57) ABSTRACT

The present invention relates to an improved process for the production of 1,3,3-trimethyl-2-(3-methylpent-2-en-4-ynyl)cyclohex-1-ene, highly enriched in the Z-isomer, and the use of such compounds in organic syntheses, especially in processes forming intermediates (building blocks) the synthesis of vitamin A or β-carotene or other carotenoids, e.g. canthaxanthin, astaxanthin or zeaxanthin.

9 Claims, No Drawings

PROCESS FOR THE PRODUCTION OF 1,3,3-TRIMETHYL-2-(3-METHYLPENT-2-EN-4-YNYL)CYCLOHEX-1-ENE

This application is the U.S. national phase of International Application No. PCT/EP2012/061280 filed 14 Jun. 2012 which designated the U.S. and claims priority to EP Patent Application No. 11171068.7 filed 22 Jun. 2011, the entire contents of each of which are hereby incorporated by reference.

The present invention relates to an improved process for the production of 1,3,3-trimethyl-2-(3-methylpent-2-en-4-ynyl)cyclohex-1-ene, as well as to an isomerically highly enriched form thereof and the use of such compounds in organic syntheses, especially in processes forming intermediates (building blocks) for the synthesis of vitamin A or β-carotene or other carotenoids, e.g. canthaxanthin, zeaxanthin or astaxanthin. Especially to be mentioned is that the new compounds are useful as starting materials for the synthesis of vitamin A.

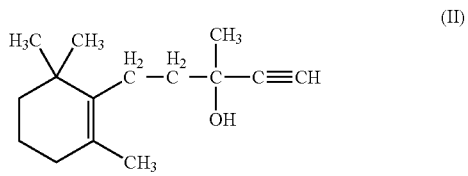

Vitamin A (all-E)-retinol (vitamin A)

is an important ingredient for many applications. Vitamin A plays a role in a variety of functions throughout the body, such as e.g. vision process, gene transcription, immune function, bone metabolism, haematopoiesis, skin and cellular health and antioxidant function. Due to the importance of vitamin A (and its derivatives) and the complexity of the synthesis thereof, there is always a need for improved processes of production.

1,3,3-trimethyl-2-(3-methylpent-2-en-4-ynyl)cyclohex-1-ene, the compound of formula (I)

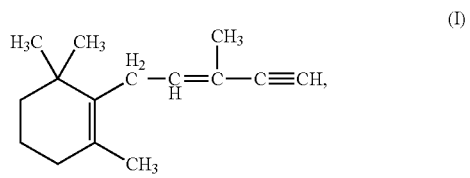

(I)

is an important compound in organic synthesis. Compounds of formula (I) are used e.g. in the synthesis of intermediates which are used in the synthesis of vitamin A or β-carotene.

G. Ohloff et al. have demonstrated that the synthesis of compound of formula (I) by dehydration of compound (II) is not trivial as under typical (acidic) dehydration conditions (using e.g. p-toluenesulfonic acid, perchloric acid or formic acid) compound (II) was found to form the cyclisation products (A') and (B') (K. H. Schulte-Elte, T. Umiker, G. Ohloff, *Helv. Chim. Acta* 1980, 63, 284-292).

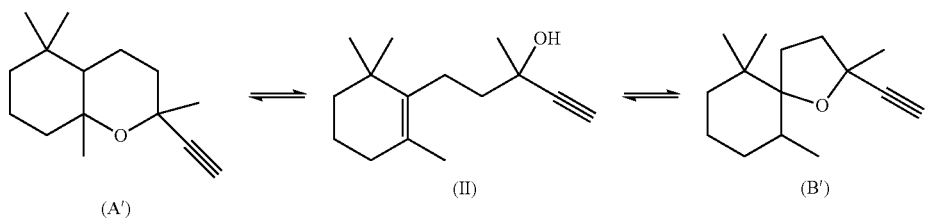

(A')  (II)  (B')

GB1034189 describes a method for the production of compound of formula (I) by dehydration of 3-methyl-5-(2,6,6-trimethylcyclohex-1-enyl)pent-1-yn-3-ol (compound of formula (II))

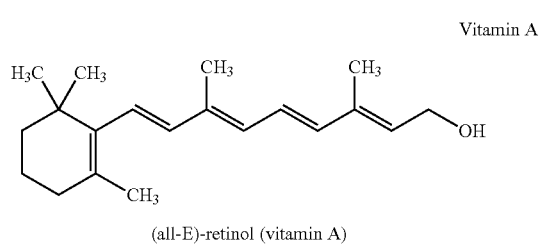

(II)

using aluminum phosphate at temperatures in the range of 230° C. to 250° C. and under reduced pressure of 20 mmHg (=2,666,45 Pa). Under these conditions the product is obtained in 70% yield. 1,3,3-trimethyl-2-(3-methylpent-2-en-4-ynyl)cyclohex-1-ene is obtained and used as a mixture of isomers.

The goal of the present invention was to find an alternative reaction for the process of production of compound of formula (I), which does not need high temperature, reduced pressure and a high amount of aluminum salt, with the aim to reduce waste formation, energy consumption, and increase the space time yield.

Surprisingly it was found that compound of formula (I) is obtained in higher yield compared to the state-of-the-art by using specific types of catalysts and working at lower temperature, atmospheric pressure and under catalytic conditions.

Therefore the present invention relates to a new and improved process of production of 1,3,3-trimethyl-2-(3-methylpent-2-en-4-ynyl)cyclohex-1-ene (compound of formula (I)) by dehydration of 3-methyl-5-(2,6,6-trimethylcyclohex-1-enyl)pent-1-yn-3-01 (compound of formula (II)), characterized in that at least one thiolate-bridged diruthenium complex is used as a catalyst.

Usually the reaction temperature is between 40° C. and 100° C., preferably 50° C. and 80° C. The process according to the present invention is carried out at ambient pressure. Thiolate-bridged diruthenium complexes are used as catalysts in the process according to the present invention. It is also possible to use mixtures of such catalyst. Preferably, a catalyst system comprising $[(C_5(CH_3)_5)RuCl(\mu_2\text{-SMe})_2Ru(C_5(CH_3)_5)Cl]$ and a weakly coordinating anion is used. Weakly coordinating anions are tetrafluoroborate, hexafluorophosphate, tetrachloroaluminate, perchlorate, tetrakis-[3, 5-bis(trifluoromethyl)phenyl]borate (BAr$_F$), methylaluminiumoxane (MAO), triflate, triflimide.

The ratio of the diruthenium complex to weakly coordinating anion used is 1:0.9 to 1:3, preferred 1:0.95 to 1:2. The ruthenium catalyst is used in a ratio of 1:200 to 1:10 with regard to the starting material (compound of formula (I)).

The process according to the present invention is carried out in a solvent. Usually, water free solvents (or mixtures of solvents) are used. Suitable solvents are polar or non-polar aprotic solvents, e.g. ethers, like THF, methyl-THF, MTBE, esters, like ethyl acetate, or 1,2-dichlorethane or dichloromethane.

A further surprising effect of the process as described above is that it yields the product of formula (I) with a large excess (more than 85%) of (Z)-1,3,3-trimethyl-2-(3-methylpent-2-en-4-ynyl)cyclohex-1-ene, which is the compound of formula of formula (Ia)

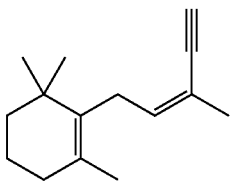

(Ia)

It is possible to remove the sideproducts (e.g. the E-isomer) to get the highly enriched Z-isomer. This can be done by using commonly known purification methods, such as e.g. column chromatography.

The present invention also relates to a new compound. The compound of formula (Ia) ((Z)-1,3,3-trimethyl-2-(3-methylpent-2-en-4-ynyl)cyclohex-1-ene) is new. Therefore the present invention also relates to the compound of formula (Ia)

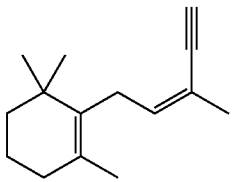

(Ia)

The structure or purity of (Z)-1,3,3-trimethyl-2-(3-methylpent-2-en-4-ynyl)cyclohex-1-ene can be determined by any commonly used analytic methods, such as NMR, GC, HPLC or TLC.

The analytical data for the new compound of formula (Ia) are as follows:

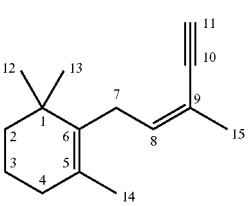

(Ia)

$^1$H-NMR (300 MHz, CDCl$_3$): δ [ppm]=0.99 (s, 6H, CH$_3$, H12+H13), 1.42 (m, 2H, CH$_2$, H2), 1.55 (m, 2H, CH$_2$, H3), 1.58 (s, 3H, CH$_3$, H14), 1.85 (s, 3H, CH$_3$, H15), 1.90 (t, J=6.3 Hz, 2H, CH$_2$, H4), 2.99 (d, J=6.8 Hz, 2H, CH$_2$, H7), 3.16 (s, 1H, CH, H11), 5.61 (t, 1H, CH, 6.8 Hz, H8).

$^{13}$C-NMR (300 MHz, CDCl$_3$): δ [ppm]=19.5 (C3), 19.8 (C14), 22.7 (C15), 28.2 (C12+C13), 30.1 (C7), 33.0 (C4), 35.0 (C1), 39.8 (C2), 80.9 (C11), 84.9 (C10), 115.5 (C9), 128.7 (C5), 135.3 (C6), 140.3 (C8).

GC (as described in Example 1): t$_R$ (Ia)=8.85 min.

HPLC (as described in Example 1): t$_R$ (Ia)=5.59 min.

TLC (SiO$_2$, cyclohexane/ethylacetate 9:1, anisaldehyde): R$_f$(Ib)=0.67.

The (E)-form of ((Z)-1,3,3-trimethyl-2-(3-methylpent-2-en-4-ynyl)cyclohex-1-ene), which is the compound of formula (Ib)

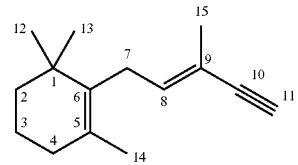

(Ib)

can be synthesized for example according to the method as described by Rey et al., Tetrahedron Letters 1993, 34(39), p. 6293-6296. The analytical data for compound of formula (Ib) are summarized below:

$^1$H-NMR (300 MHz, CDCl$_3$): δ [ppm]=0.96 (s, 6H, 2×CH$_3$, H12+H13), 1.40-1.44 (m, 2H, CH$_2$, H2), 1.53 (s, 3H, CH$_3$, H14), 1.55-1.61 (m, 2H, CH$_2$, H3), 1.84 (d, J=1.4 Hz, 3H, CH$_3$, H15), 1.92 (t, J=6.0 Hz, 2H, CH$_2$, H4), 2.74 (s, 1H, CH, H11), 2.78 (d, J=6.8 Hz, 2H, CH$_2$, H7), 5.80 (td, J=6.8 Hz, J=1.4 Hz, 1H, CH, H8).

$^{13}$C-NMR (300 MHz, CDCl$_3$): δ [ppm]=17.1 (C15), 19.5 (C3), 19.8 (C14), 27.8 (C7), 28.2 (2C, C12+C13), 33.0 (C4), 34.9 (C1), 39.7 (C2), 73.1 (C11), 87.1 (C/O), 115.1 (C9), 128.8 (C5), 135.2 (C6), 141.0 (C8).

GC (as described in Example 1): t$_R$ (Ib)=9.26 min.

HPLC (as described in Example 1): t$_R$ (Ib)=5.24 min.

TLC (SiO$_2$, cyclohexane/ethylacetate 9:1, anisaldehyde): R$_f$(Ib)=0.67.

The product of the process according to the present invention can be used in organic synthesis. It is an important product, e.g. in the synthesis of vitamin A or β-carotene, canthaxanthin, zeaxanthin or astaxanthin, especially in a process forming an intermediate (building block) for the synthesis of vitamin A or β-carotene (preferably vitamin A). Additionally, it is very interesting to have a process, which allows producing a mixture with an excess of the Z-isomer of formula (Ia).

Compounds of formula (I), which are obtainable by the process according to the present invention, are reacted with compounds of formula (III)

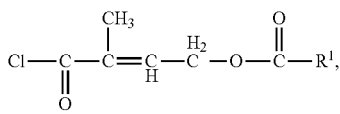

(III)

wherein R$^1$ signifies a C$_1$-C$_{15}$ alkyl moiety or a C$_2$-C$_{18}$ alkenyl moiety.

When R$^1$ is a C$_1$-C$_{15}$ alkyl moiety, then preferably the alkyl moiety is linear. Especially preferred alkyl moieties are methyl, ethyl and pentadecyl. When $R^1$ is a $C_2$-$C_{18}$ alkenyl moiety, compounds of formula (III) contain two or more C—C double bonds. Preferably the alkenyl moiety is unbranched.

The reaction products thereof (compounds of formula (IV))

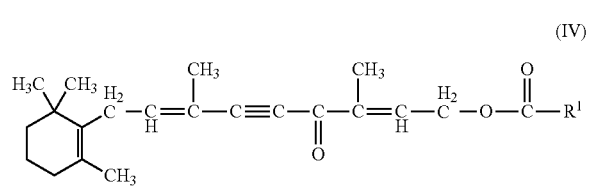

are intermediates for the synthesis of vitamin A or β-carotene or other carotenoids e.g. canthaxanthin, astaxanthin and zeaxanthin, especially for the synthesis of vitamin A (and its derivatives). Compounds of formula (III) are new compounds.

The compounds of formula (III) can be produced by chlorination of compounds of formula (V)

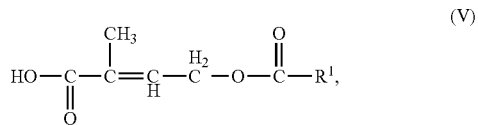

wherein $R^1$ signifies a $C_1$-$C_{15}$ alkyl moiety or a $C_2$-$C_{18}$ alkenyl moiety and wherein at least one chlorination reactant is used.

When $R^1$ is a $C_1$-$C_{15}$ alkyl moiety, then preferably the alkyl moiety is linear. Especially preferred alkyl moieties are methyl, ethyl and pentadecyl.

When $R^1$ is a $C_2$-$C_{18}$ alkenyl moiety, compounds of formula (V) contain two or more C—C double bonds. Preferably the alkenyl moiety is unbranched.

Chlorination reactants are widely known and used. For the production of compounds of formula (III) any chlorination reactant (or mixtures thereof) can be used. Examples of chlorination reactants are oxalylchloride, phosphorus pentachloride, thionylchloride, phosphorus oxychloride, chlorine, chloric acid, antimony(V) chloride, hypochlorous acid, N-chlorosuccinimide, phosphorus trichloride, sulfurylchloride, carbon tetrachloride, cyanuric chloride. Preferred chlorination reactants are oxalylchloride, phosphorus pentachloride, thionylchloride and phosphorus oxychloride.

The chlorination reactants are usually added in a slight molar excess in regard to the amount of compound of formula (V). The reaction is usually carried out in a polar or non-polar solvents like toluene, N,N-dimethylformamide (DMF), dichloromethane, dichloroethane, 1-methyl-2-pyrrolidone (NMP), xylenes, or ethers. The chlorination of the compounds of formula (V) is usually carried out at temperatures of from −20° C. to 100° C., preferably from 0° C. to 50° C.

The compounds of formula (IV) are used as intermediates in the synthesis of vitamin A (and its derivatives) and β-carotene, preferably in the synthesis vitamin A (and its derivatives).

The present examples serve to illustrate the present invention.

EXAMPLES

Example 1

(Z)-1,3,3-trimethyl-2-(3-methylpent-2-en-4-ynyl) cyclohex-1-ene (compound of formula (Ia))

Under nitrogen atmosphere, 16.1 mg (0.03 mmol, 5 mol-%) of [(C$_5$(CH$_3$)$_5$)RuCl(μ$_2$-SMe)$_2$Ru(C$_5$(CH$_3$)$_5$)Cl] and 5.3 mg (0.05 mmol) of ammonium tetrafluoroborate were dissolved in 7.5 ml of anhydrous 1,2-dichloroethane. To the dark red solution was added drop wise at room temperature a solution of 129 mg (0.5 mmol) of 3-methyl-5-(2,6,6-trimethylcyclohex-1-enyl)pent-1-yn-3-ol (compound of formula (II)) in 5.0 ml of anhydrous 1,2-dichloroethane. After complete addition of the starting material, the solution was heated to 60° C. After 3 hours at 60° C. the brown solution was cooled to room temperature.

The reaction mixture was washed with half-concentrated brine (3×25 ml). The aqueous layers were extracted twice with 20 ml of dichloromethane. The combined organic layers were dried over sodium sulphate and concentrated to dryness. The crude product (compound of formula (I)) was obtained in 93% yield with a Z/E ratio of 93:7. By-product (VI) was not detected.

Analytical data of crude product (E/Z mixture=mixture of compound of formula (Ia) and Ib):

Ia:
$^1$H-NMR (300 MHz, CDCl$_3$): δ [ppm]=0.99 (s, 6H, CH$_3$, H12+H13), 1.42 (m, 2H, CH$_2$, H2), 1.55 (m, 2H, CH$_2$, H3), 1.58 (s, 3H, CH$_3$, H14), 1.85 (s, 3H, CH$_3$, H15), 1.90 (t, J=6.3 Hz, 2H, CH$_2$, H4), 2.99 (d, J=6.8 Hz, 2H, CH$_2$, H7), 3.16 (s, 1H, CH, H11), 5.61 (t, 1H, CH, 6.8 Hz, H8).
$^{13}$C-NMR (300 MHz, CDCl$_3$): δ [ppm]=19.5 (C3), 19.8 (C14), 22.7 (C15), 28.2 (C12+C13), 30.1 (C7), 33.0 (C4), 35.0 (C1), 39.8 (C2), 80.9 (C11), 84.9 (C10), 115.5 (C9), 128.7 (C5), 135.3 (C6), 140.3 (C8).
GC: $t_R$ (II)=9.84 min, $t_R$ (Ia)=8.85 min.
HPLC: $t_R$ (II)=3.17 min, $t_R$ (Ia)=5.59 min.
TLC (SiO$_2$, cyclohexane/ethylacetate 9:1, anisaldehyde); $R_f$(II)=0.16, $R_f$(Ia)=0.63.

Ib:
$^1$H-NMR (300 MHz, CDCl$_3$): δ [ppm]=0.96 (s, 6H, 2×CH$_3$, H12+H13), 1.40-1.44 (m, 2H, CH$_2$, H2), 1.53 (s, 3H, CH$_3$, H14), 1.55-1.61 (m, 2H, CH$_2$, H3), 1.84 (d, J=1.4 Hz, 3H, CH$_3$, H15), 1.92 (t, J=6.0 Hz, 2H, CH$_2$, H4), 2.74 (s, 1H, CH, H11), 2.78 (d, J=6.8 Hz, 2H, CH$_2$, H7), 5.80 (td, J=6.8 Hz, J=1.4 Hz, 1H, CH, H8).
$^{13}$C-NMR (300 MHz, CDCl$_3$): δ [ppm]=17.1 (C15), 19.5 (C3), 19.8 (C14), 27.8 (C7), 28.2 (2C, C12+C13), 33.0 (C4), 34.9 (C1), 39.7 (C2), 73.1 (C11), 87.1 (C10), 115.1 (C9), 128.8 (C5), 135.2 (C6), 141.0 (C8).
GC (as described in Example 1): $t_R$ (Ib)=9.26 min.
HPLC (as described in Example 1): $t_R$ (Ib)=5.24 min
TLC (SiO$_2$, cyclohexane/ethylacetate 9:1, anisaldehyde): $R_f$(Ib)=0.67.

The compound of formula (Ia) was purified in a final step.

GC-Method:
Instrument: Agilent 7890A; carrier gas: helium; pressure: 25 psi; flow: 88 ml/min; injection volume: 1 μl; injector: Split (10:1); injector temperature: 250° C.; column: HP-5 (5% phenyl methyl siloxane) (30 m×320 μm×0.25 μm); temperature program: 50° C. (2 min), 15° C./min, 300° C. (5 min); detector: FID; detector temperature: 300° C.

HPLC-Method:
Instrument: Agilent 1050; column: Supelcosil LC-18 (250 mm×4.6 mm×5 μm); autosampler: Agilent 1100; injector volume: 2 μl; eluent: acetonitrile/water 90:10; flow: 1.5 ml/min; temperature: 23° C.; detector: variable wavelength detector; detection wavelength: 230 nm.

Example 2

(Z)-1,3,3-trimethyl-2-(3-methylpent-2-en-4-ynyl)cyclohex-1-ene (compound of formula (Ia))

Under nitrogen atmosphere, 16.1 mg (0.03 mmol, 5 mol-%) of $[(C_5(CH_3)_5)RuCl(\mu_2\text{-}SMe)_2Ru(C_5(CH_3)_5)Cl]$ were dissolved in 7.5 ml of anhydrous 1,2-dichloroethane. To the dark red solution was added drop wise at room temperature a solution of 129 mg (0.5 mmol) of 3-methyl-5-(2,6,6-trimethylcyclohex-1-enyl)pent-1-yn-3-ol (compound of formula (II)) in 5.0 ml of anhydrous 1,2-dichloroethane. After complete addition of the starting material, the solution was heated to 60° C. After 24 hours at 60° C. the brown solution was cooled to room temperature.

The reaction mixture was washed with half-concentrated brine (3×25 ml). The aqueous layers were extracted twice with 20 ml of dichloromethane. The combined organic layers were dried over sodium sulphate and concentrated to dryness. The crude product (compound of formula (I)) was obtained in 91% yield with a Z/E ratio of 87:13. By-product (VI) was not detected. For analytical data see Example 1.

Example 3

3,7-dimethyl-4-oxo-9-(2,6,6-trimethylcyclohex-1-enyl)nona-2,7-dien-5-ynyl acetate (compound of formula (IVa))

Under nitrogen atmosphere 59.9 mg (0.308 mmol) of copper(I) iodide and 110.3 mg (0.154 mmol) of bis(triphenylphosphine)palladium(II) dichloride $[(PPh_3)_2PdCl_2]$ were added to a 100 ml four-necked flask. At 23° C., 42.0 ml of anhydrous THF were added and the yellow suspension was stirred for 5 min. When 2.15 ml (15.4 mmol) of triethylamine were introduced dropwise via syringe an orange solution was obtained. Within 1 minute 3.10 g (15.4 mmol) of 4-chloro-3-methyl-4-oxobut-2-enyl acetate (compound of formula (IIIa))

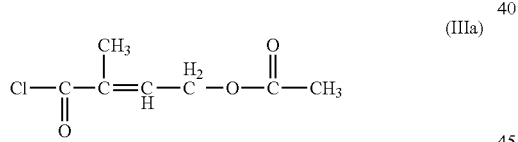
(IIIa)

were added and the solution turned dark orange. Upon drop wise addition of 2.92 g (14.0 mmol) of the reaction product of Example 1 over 5 minutes a yellow suspension was formed. The reaction mixture was cooled to room temperature and monitored by GC and TLC. After 2 hours and 20 min at 23° C., all starting material was consumed. The reaction mixture was transferred into a separatory funnel, diluted with 80 ml of diethyl ether and washed with semi-concentrated sodium bicarbonate solution (80 ml). The layers were separated and the aqueous layer was extracted with diethyl ether (2×75 ml). The combined organic layers were washed with 80 ml of semi-sat. sodium bicarbonate solution, dried over sodium sulphate and concentrated to dryness. The crude product (compound of formula (IVa))

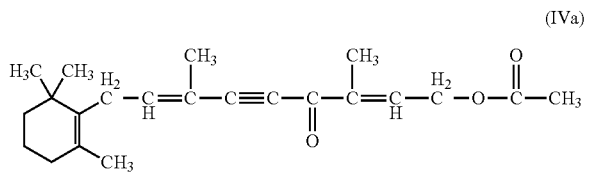 [SMILES: CC(=O)OCC=C(C)C(=O)C#CC(C)=CCC1=C(C)CCCC1(C)C]
(IVa)

was obtained as brown oil (5.44 g, 82% purity, 93% yield) and purified by column chromatography and charcoal treatment.

Comparison Example 1

To a solution of 26 mg (0.13 mmol) of 3-methyl-5-(2,6,6-trimethylcyclohex-1-enyl)pent-1-yn-3-ol (compound of formula (II)) in 1.0 ml of anhydrous toluene were added 94 mg of Amberlyst-15. After stirring at 23° C. for 48 hours the acidic ion exchange resin was removed by filtration and the solvent was evaporated under reduced pressure. GC analysis of the crude product showed 65 area-% of compound of formula (A'). Product A' was identified by comparison with reference NMR data (see G. Ohloff et al., *Helvetica Chimica Acta* 1976, 59, 1158-1168).

Comparison Example 2

Under nitrogen atmosphere, 54.2 mg (0.085 mmol, 0.625 mol-%) of $[(C_5(CH_3)_5)RuCl(\mu_2\text{-}SMe)_2Ru(C_5(CH_3)_5)Cl]$ and 143.3 mg (1.367 mmol, 10 mol-%) of ammonium tetrafluoroborate were dissolved in 80 ml of anhydrous 1,2-dichloroethane. To the dark red solution was added drop wise at room temperature a solution of 3.369 g (13.67 mmol) of 3-methyl-5-(2,6,6-trimethylcyclohex-1-enyl)pent-1-yn-3-ol (compound of formula (II)) in 5.0 ml of anhydrous 1,2-dichloroethane.

After complete addition of the starting material, the solution was heated to 60° C. After 3 hours at 60° C. the brown solution was cooled to room temperature. The reaction mixture was washed with half-concentrated brine (3×150 ml). The aqueous layers were extracted twice with 150 ml of dichloromethane. The combined organic layers were dried over sodium sulphate and concentrated to dryness. The crude product (compound of formula (I)) was obtained in 81% yield with a Z/E ratio of 94:6 together with 15% yield of 1,3,3-trimethyl-2-(3-methylenepent-4-ynyl)cyclohex-1-ene (compound of formula (VI)) as undesired by-product.

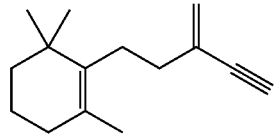
(VI)

The invention claimed is:

1. A process of production of 1,3,3-trimethyl-2-(3-methylpent-2-en-4-ynyl)cyclohex-1-ene according to formula (I):

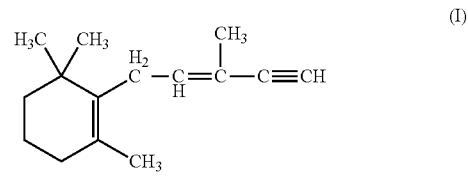
(I)

wherein the process comprises dehydrating 3 methyl-5-(2,6,6-trimethylcyclohex-1-enyl)pent-1-yn-3-ol according to formula (II):

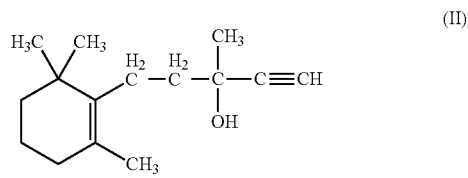 [SMILES: C#CC(C)(O)CCC1=C(C)CCCC1(C)C]
(II)

in the presence of at least one thiolate-bridged diruthenium complex as catalyst.

2. The process according to claim 1, wherein the process is carried out at a temperature of between 40° C. and 100° C.

3. The process according to claim 1, wherein the process is carried out at ambient pressure.

4. The process according to claim 1, wherein the process is carried out using a catalyst system comprising thiolate-bridged diruthenium complexes and optionally a weakly coordinating anion.

5. The process according to claim 1, wherein the process is carried out using a catalyst system comprising $(C_5(CH_3)_5)RuCl(\mu_2\text{-}SMe)_2Ru(C_5(CH_3)_5)Cl$ and ammonium tetrafluoroborate.

6. The process according to claim 1, wherein the process is carried out in a water-free solvent.

7. The process according to claim 1, wherein the process yields a large excess of more than 85% of (Z)-1,3,3-trimethyl-2-(3-methylpent-2-en-4-ynyl)cyclohex-1-ene according to formula (Ia):

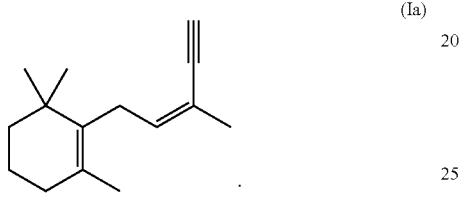

(Ia)

8. The process according to claim 1, wherein the process is carried out at a temperature of between 50° C. and 80° C.

9. The process according to claim 1, wherein the process is carried out in a mixture of solvents.

* * * * *